United States Patent
Okui et al.

(10) Patent No.: US 6,335,357 B1
(45) Date of Patent: *Jan. 1, 2002

(54) PYRAZOLE DERIVATIVES, PROCESS FOR PREPARING THE SAME, INTERMEDIATES, AND PEST CONTROL AGENT CONTAINING THE SAME AS ACTIVE INGREDIENT

(75) Inventors: Shuko Okui; Nobuo Kyomura; Toshiki Fukuchi; Ken Tanaka, all of Kanagawa (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,454

(22) PCT Filed: Apr. 6, 1998

(86) PCT No.: PCT/JP98/01582

§ 371 Date: Oct. 7, 1999

§ 102(e) Date: Oct. 7, 1999

(87) PCT Pub. No.: WO98/45274

PCT Pub. Date: Oct. 15, 1998

(30) Foreign Application Priority Data

Apr. 7, 1997 (JP) ............................................. 9-087916

(51) Int. Cl.$^7$ ...................... A01N 43/56; C07D 231/44; C07D 401/12

(52) U.S. Cl. .................. 514/404; 546/275.4; 546/276.1; 548/186; 548/205; 548/364.1; 548/364.4; 548/364.7; 548/365.1; 548/365.7; 548/367.4

(58) Field of Search .............................. 548/365.7, 367.4; 546/276.1, 275.4; 514/404

(56) References Cited

U.S. PATENT DOCUMENTS

| | | |
|---|---|---|
| 5,580,843 A | 12/1996 | Stetter et al. |
| 5,883,112 A | 3/1999 | Pilato et al. |

FOREIGN PATENT DOCUMENTS

| | | |
|---|---|---|
| JP | 10-7509 | of 1988 |
| JP | 64-47768 | * 2/1989 |
| WO | WO 97/42815 | 11/1997 |
| WO | WO 00/31066 | 6/2000 |

* cited by examiner

Primary Examiner—Robert W. Ramsuer
(74) Attorney, Agent, or Firm—Oblon, Spivak, McClelland, Maier & Neustadt, P.C.

(57) ABSTRACT

A 1-aryl-3-cyano-5-(het)arylalkylaminopyrazole derivative represented by the general formula (1):

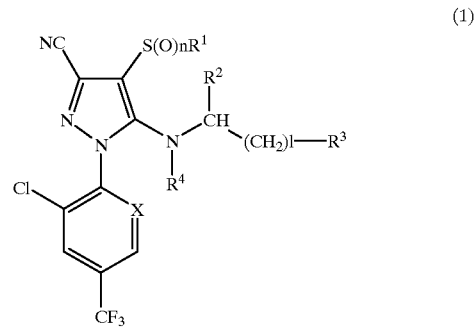

(1)

process of making, intermediate thereof and pesticide therewith.

21 Claims, No Drawings

PYRAZOLE DERIVATIVES, PROCESS FOR PREPARING THE SAME, INTERMEDIATES, AND PEST CONTROL AGENT CONTAINING THE SAME AS ACTIVE INGREDIENT

TECHNICAL FIELD

This invention relates to a novel 1-aryl-3-cyano-5-(het)arylalkylaminopyrazole derivative and a pesticide containing the same as an active ingredient, such as an agricultural and horticultural insecticide.

BACKGROUND ART

In the agricultural and horticultural field, a wide variety of insecticides have been developed and put to practical use for the purpose of controlling various harmful insects.

Pyrazole compounds known to have insecticidal activity include 5-(substituted)amino-3-cyano-1-phenylpyrazole derivatives disclosed in an unexamined published Japanese patent application 63-316771, 1-aryl-5-(het)arylmethylaminopyrazole derivatives disclosed in an unexamined published Japanese patent application 64-47768, and 1-aryl-3-cyano-5-(het)arylmethylideneiminopyrazole derivatives disclosed in an unexamined published Japanese patent application 5-148240.

However, these agricultural and horticultural insecticides are not necessarily satisfactory in all of insecticidal effect, insecticidal spectrum, safety, and the like.

Emergence of strains of harmful insects which have acquired resistance to the commercially available insecticides has now become a serious problem. For example, various insects having developed resistance to various types of pesticides (e.g., organophosphorus compounds), have come out in various sites of cultivation of vegetables, fruits, flowers, teas, wheat, rice, etc. Control of various pests caused by these insect pests is becoming increasingly difficult year by year, and development of a novel pesticide based on a unique skeleton has been awaited.

While there are some pesticides to which pathogens or insect pests have not yet acquired resistance, such as dithiocarbamate compounds and phthalimide compounds, they are not preferred from the viewpoint of environmental pollution because, in general, they should be applied in large amounts or frequently.

Accordingly, it has been keenly demanded to develop a novel pesticide which exhibits an excellent insecticidal effect, a broad insecticidal spectrum, and high safety with reduced influences on the environment.

An object of the present invention is to provide a novel pesticide which exhibits an excellent insecticidal effect, a broad insecticidal spectrum, and high safety with reduced influences on the environment. More specifically, it is an object of the invention to provide 1-aryl-3-cyano-5-(het)arylalkylaminopyrazole derivatives having the above usefulness and a process for synthesizing them efficiently.

DISCLOSURE OF THE INVENTION

As a result of extensive investigations, the inventor of the present invention has found that a novel pyrazole compound represented by the formula shown below is the compound that possesses the above-mentioned characteristics and thus completed the present invention. Thus, the gist of the invention lies in a 1-aryl-3-cyano-5-(het)arylalkylaminopyrazole derivative represented by the general formula (1):

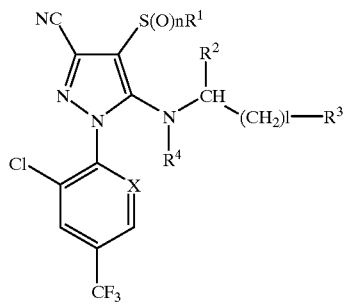

wherein $R^1$ represents an alkyl group having 1 to 4 carbon atoms (hereinafter the carbon atom number will be expressed like "C1–C4") or a C1–C8 haloalkyl group; $R^2$ represents a hydrogen atom or a C1–C4 alkyl group; $R^3$ represents an aryl or heteroaryl group which may be substituted with a substituent selected from a hydrogen atom, a hydroxyl group, a C1–C4 alkyl group, a C1–C8 haloalkyl group, a C1–C4 alkoxy group, a phenoxy group which may be substituted, a C1–C4 haloalkoxy group, a C1–C4 alkylthio group, a C1–C4 alkylsulfinyl group, a C1–C4 alkylsulfonyl group, a halogen atom, a nitro group, and a cyano group; and $R^4$ represents a hydrogen atom, a C1–C4 alkyl group or a C1–C5 acyl group; X represents a nitrogen atom or a halogen-substituted carbon atom; and 1 and n each independently represent 0, 1 or 2; a process for producing the same; an intermediate for preparing the same, being represented by the following general formula (3):

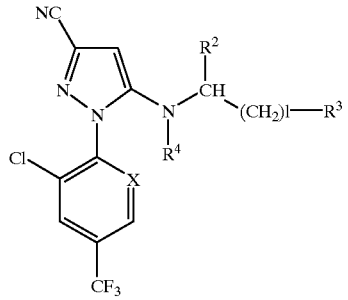

wherein $R^2$, $R^3$, $R^4$, X, and 1 are as defined above; and use as a pesticide.

BEST MODES FOR CARRYING OUT THE INVENTION

The present invention will be described in detail.

In the compounds represented by the general formula (1), $R^1$ represents a C1–C4 straight-chain or branched alkyl group, such as a methyl group, an ethyl group, an n-propyl group, an isopropyl group, an n-butyl group, an isobutyl group, a sec-butyl group or a t-butyl group; or a C1–C8 straight-chain or branched haloalkyl group, such as a difluoromethyl group, a trifluoromethyl group, a 2-fluoroethyl group, a 2-chloroethyl group, a 2,2,2-trifluoroethyl group, a 2,2,2-trichloroethyl group, a 3-chloropropyl group, a 3-bromopropyl group, a 3,3,3-trifluoropropyl group, a 2,2,3,3,3-pentafluoropropyl group, a 2,2-dichloro-3,3,3-trifluoropropyl group, a 1,3-difluoro-2-propyl group, a 1,1,1,3,3,3-hexafluoro-2-propyl group, a 3,3,3-trichloropropyl group, a 4-chlorobutyl group, a 4,4,4-trifluorobutyl group, a 3,3,4,4,4-pentafluorobutyl group, a 5,5,5-trifluoropentyl group or a 6,6,6-trifluorohexyl group. Preferred of them is a C1–C4 alkyl group or a C1–C4 haloalkyl group.

$R^2$ represents a hydrogen atom; or a C1–C4 straight-chain or branched alkyl group, such as a methyl group, an ethyl group, an n-propyl group, an isopropyl group, an n-butyl group, an isobutyl group, a sec-butyl group or a t-butyl group. Preferred of them is a hydrogen atom.

$R^3$ is an aryl group, such as a phenyl group or a naphthyl group, or a heteroaryl group having 3 to 8 carbon atoms and 1 to 3 hetero atom(s) arbitrarily selected from a nitrogen atom, an oxygen atom and a sulfur atom. These groups may be arbitrarily substituted with substituent $R^5$ described below. Examples of them include:

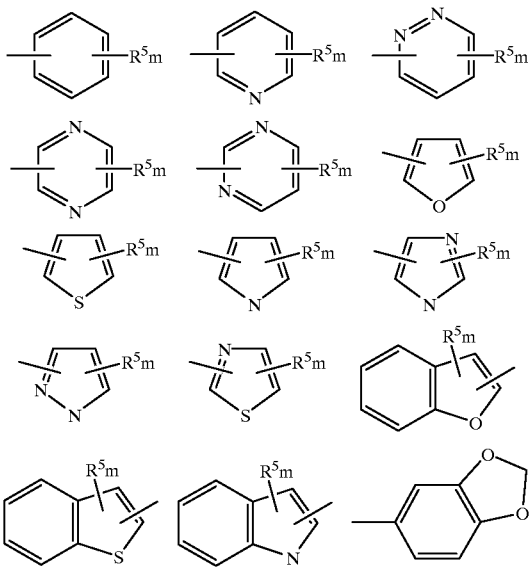

wherein $R^5$ represents a hydrogen atom, a hydroxyl group, a C1–C4 alkyl group, a C1–C8 haloalkyl group, a C1–C4 alkoxy group, a phenoxy group which may be substituted, a C1–C4 haloalkoxy group, a C1–C4 alkylthio group, a C1–C4 alkylsulfinyl group, a C1–C4 alkylsulfonyl group, a halogen atom, a nitro group, or a cyano group; and m represents 0, 1 or 2.

Preferred of them are:

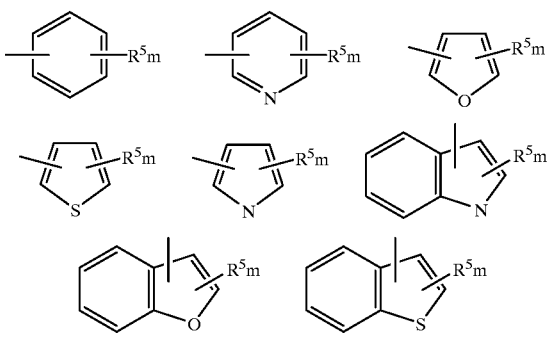

wherein $R^5$ and m are as defined above.

Still preferred are:

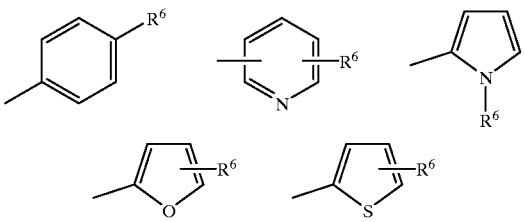

wherein $R^6$ represents a hydrogen atom, a hydroxyl group, a C1–C2 alkyl group, a C1–C2 alkoxy group, a C1–C2 haloalkoxy group, a C1–C2 alkylthio group, a halogen atom, a nitro group, or a cyano group.

$R^5$ represents a hydrogen atom; a hydroxyl group; a C1–C4 straight-chain or branched alkyl group, such as a methyl group, an ethyl group, an n-propyl group, an isopropyl group, an n-butyl group, an isobutyl group, a sec-butyl group or a t-butyl group; a C1–C8 straight-chain or branched haloalkyl group, such as a difluoromethyl group, a trifluoromethyl group, a 2-fluoroethyl group, a 2-chloroethyl group, a 2,2,2-trifluoroethyl group, a 2,2,2-trichloroethyl group, a 3-chloropropyl group, a 3-bromopropyl group, a 3,3,3-trifluoropropyl group, a 2,2,3,3-tetrafluoropropyl group, a 2,2,3,3,3-pentafluoropropyl group, a 2,2-dichloro-3,3,3-trifluoropropyl group, 2,2-dichloro-3,3,3-trifluoropropyl group, a 1,3-difluoro-2-propyl group, a 1,1,1,3,3,3-hexafluoro-2-propyl group, a 3,3,3-trichloropropyl group, a 4-chlorobutyl group, a 4,4,4-trifluorobutyl group, a 3,3,4,4,4-pentafluorobutyl group, 5-chloropentyl group, or a 6,6,6-trifluorohexyl group; a C1–C4 straight-chain or branched alkoxy group, such as a methoxy group, an ethoxy group, an n-propoxy group, an isopropoxy group, an n-butoxy group, an isobutoxy group, a sec-butoxy group, or a t-butoxy group; a phenoxy group which may be substituted with a C1–C4 alkoxy group or a C1–C4 alkyl group; a C1–C4 straight-chain or branched haloalkoxy group, such as a difluoromethoxy group, a trifluoromethoxy group, a 2-fluoroethoxy group, a 2-chloroethoxy group, a 2,2,2-trifluoroethoxy group, a 2,2,2-trichloroethoxy group, a 3-chloropropoxy group, a 3-bromopropoxy group, a 3,3,3-trifluoropropoxy group, a 2,2,3,3-tetrafluoropropoxy group, a 2,2,3,3,3-pentafluoropropoxy group, a 2,2-dichloro-3,3,3-trifluoropropoxy group, a 2,2-dichloro-3,3,3-trifluoropropoxy group, a 1,3-difluoro-2-propoxy group, a 1,1,1,3,3,3-hexafluoro-2-propoxy group, a 3,3,3-trichloropropoxy group, a 4-chlorobutoxy group, a 4,4,4-trifluorobutoxy group, or a 3,3,4,4,4-pentafluorobutoxy group; a C1–C4 straight-chain or branched alkylthio group, such as a methylthio group, an ethylthio group, an n-propylthio group, an isopropylthio group, an n-butylthio group, an isobutylthio group, a sec-butylthio group, or a t-butylthio group; a C1–C4 straight-chain or branched alkylsulfinyl group, such as a methylsulfinyl group, an ethylsulfinyl group, an n-propylsulfinyl group, an isopropylsulfinyl group, an n-butylsulfinyl group, an isobutylsulfinyl group, a sec-butylsulfinyl group, or a t-butylsulfinyl group; a C1–C4 straight-chain or branched alkylsulfonyl group, such as a methylsulfonyl group, an ethylsulfonyl group, an n-propylsulfonyl group, an isopropylsulfonyl group, an n-butylsulfonyl group, an isobutylsulfonyl group, a sec-butylsulfonyl group, or a t-butylsulfonyl group; a halogen atom; a nitro group; or a cyano group. Preferred of them are a hydrogen atom, a hydroxyl group, a C1–C4 straight-chain or branched alkyl group, a C1–C4 straight-chain or branched alkoxy group, a C1–C4 straight-chain or branched haloalkoxy group, a C1–C4 straight-chain or branched alkylthio group, a nitro group, or a cyano group.

$R^6$ represents a hydrogen atom; a hydroxyl group; a methyl group or an ethyl group; a methoxy group or an ethoxy group; a C1–C2 haloalkoxy group, such as a difluoromethoxy group, a trifluoromethoxy group, a 2-fluoroethoxy group, a 2-chloroethoxy group, a 2,2,2-trifluoroethoxy group or a 2,2,2-trichloroethoxy group; a C1–C2 straight-chain or branched alkylthio group, such as a methylthio group, an ethylthio group, an n-propylthio group, an isopropylthio group, an n-butylthio group, an isobutylthio group, a sec-butylthio group, or a t-butylthio group; a halogen atom; a nitro group; or a cyano group.

$R^4$ represents a hydrogen atom, a C1–C4 straight-chain or branched alkyl group, such as a methyl group, an ethyl group, an n-propyl group, an isopropyl group, an n-butyl group, an isobutyl group, a sec-butyl group or a t-butyl group; or a C1–C5 straight-chain or branched acyl group, such as a methylcarbonyl group, an ethylcarbonyl group, an n-propylcarbonyl group, an isopropylcarbonyl group, an n-butylcarbonyl group, an isobutylcarbonyl group, a sec-butylcarbonyl group, or a t-butylcarbonyl group. Preferred of them are a hydrogen atom, a C1–C4 straight-chain alkyl group or a C1–C4 straight-chain acyl group.

Among the compounds of the present invention, preferred are those represented by the general formula (2):

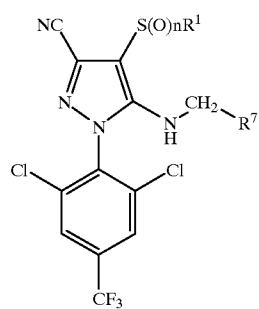

(2)

wherein $R^1$ and n are as defined above; $R^7$ represents

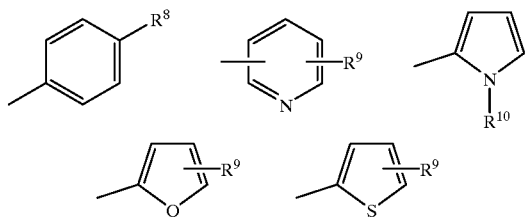

$R^8$ represents a C1–C2 alkoxy group, a C1–C2 haloalkoxy group, a C1–C2 alkylthio group, a nitro group or a cyano group; $R^9$ represents a hydrogen atom, a hydroxyl group, a C1–C2 alkoxy group, a C1–C2 haloalkoxy group or a nitro group; and $R^{10}$ represents a C1–C2 alkyl group.

Still preferred are the compounds in which $R^7$ is

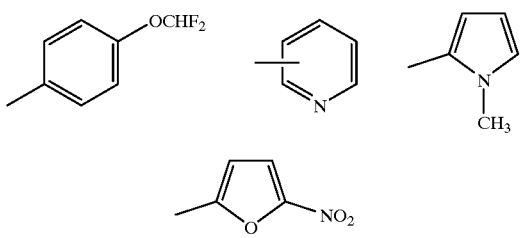

In the above-described compound, the substituent $R^8$ represents a methoxy group or an ethoxy group; a C1–C2 haloalkoxy group, such as a difluoromethoxy group, a trifluoromethoxy group, a 2-fluoroethoxy group, a 2-chloroethoxy group, a 2,2,2-trifluoroethoxy group or a 2,2,2-trichloroethoxy group; a methylthio group or an ethylthio group; a nitro group; or a cyano group.

$R^9$ represents a hydrogen atom; a hydroxyl group; a C1–C2 haloalkoxy group, such as a difluoromethoxy group, a trifluoromethoxy group, a 2-fluoroethoxy group, a 2-chloroethoxy group, a 2,2,2-trifluoroethoxy group or a 2,2,2-trichloroethoxy group; or a nitro group.

$R^{10}$ represents a methyl group or an ethyl group.

The compounds represented by the general formula (1) are prepared, for example, in accordance with the following reaction schemes 1 to 3:

Reaction Scheme 1

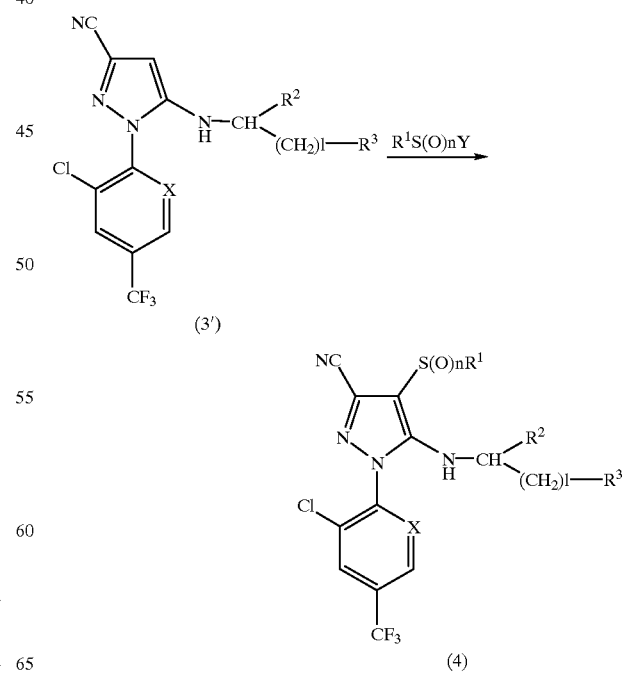

Reaction Scheme 2

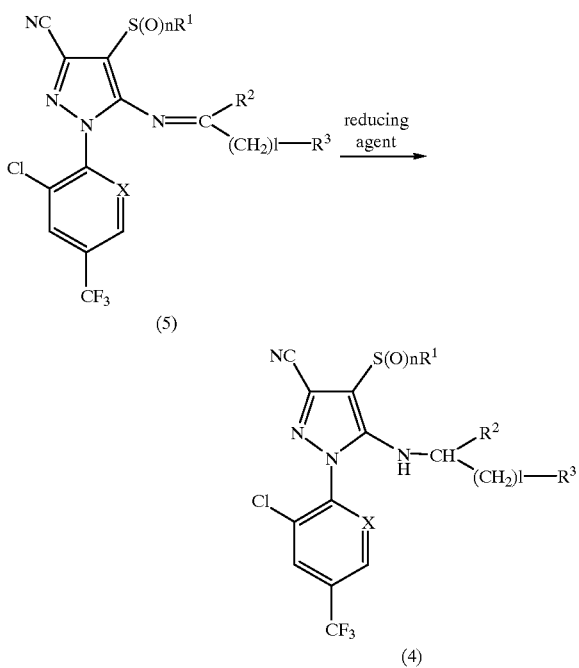

(5)

(4)

Reaction Scheme 3

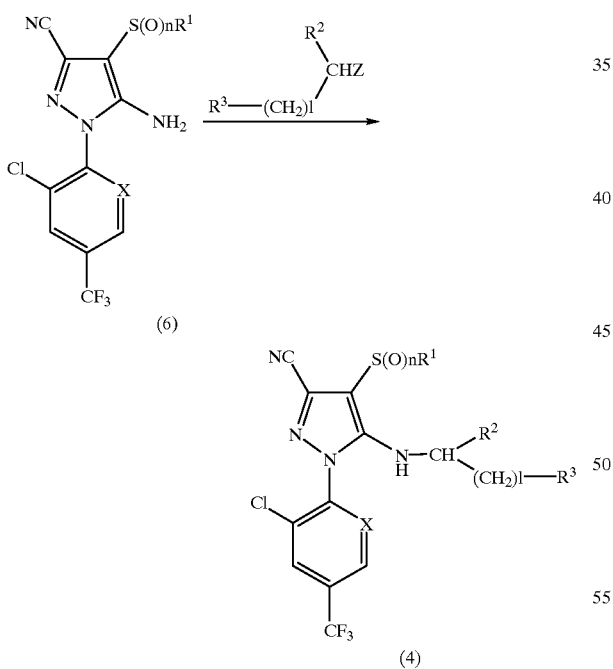

(6)

(4)

wherein $R^1$, $R^2$, $R^3$, X, l, and n are as defined above; Y represents a halogen atom, a hydroxyl group or a salt thereof, or a dialkylamino group; and Z represents a releasable group, such as a halogen atom, a hydroxyl group, etc.

The process of reaction scheme 1 is characterized in that $S(O)_nR^1$ is introduced into the compound of the general formula (3).

This reaction is carried out by allowing $R^1S(O)_n$—Y (wherein Y and n are as defined above) to react on the compound of the general formula (3) in a solvent in the presence of, if desired, a base at 0° to 150° C., preferably 0 to 100° C. Bases useful in the reaction include the tosylate of an amine compound, e.g., dimethylamine or pyridine, and commonly used inorganic bases such as alkali metal carbonates. The base is used in an amount of 0.5 to 2.0 molar equivalents, preferably 0.8 to 1.5 molar equivalents to the compound (3').

Solvents useful in the reaction include aromatic hydrocarbons such as benzene, toluene and xylene; ketones such as acetone and methyl ethyl ketone; halogenated hydrocarbons such as chloroform and methylene chloride; and polar solvents such as tetrahydrofuran and N,N-dimethylformamide.

According to necessity, $R^4$ is introduced to the nitrogen atom either before or after the above reaction. For example, the compound (3) is obtained by allowing $R^4Z$ (wherein Z represents a releasable group, e.g., a halogen atom, a hydroxyl group, etc.) to react on the compound (3') or an alkali metal derivative thereof in a solvent in the presence or absence of a base at 0° to 150° C. Solvents useful in this reaction include aromatic hydrocarbons such as benzene, toluene and xylene; ketones such as acetone and methyl ethyl ketone; halogenated hydrocarbons such as chloroform and methylene chloride; tetrahydrofuran, and N,N-dimethylformamide.

Bases useful in this reaction include organic bases such as pyridine and triethylamine and alkali metal carbonates.

The compound represented by the general formula (3) is prepared by, for example, according to the following reaction schemes 4 to 7.

Reaction Scheme 4

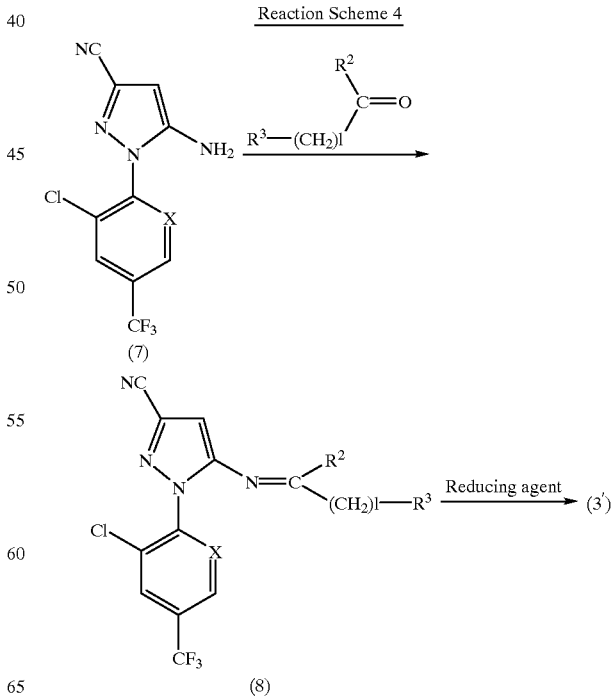

(7)

(8)

Reaction Sceme 5
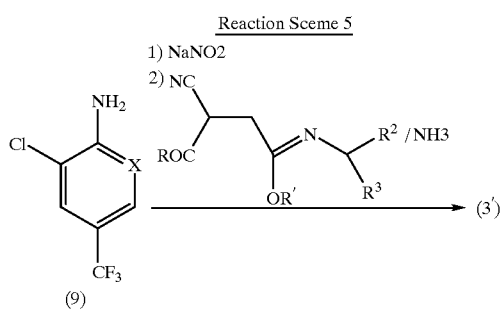
R: alkyl, alkoxy
R': alkyl
Reaction Sceme 6
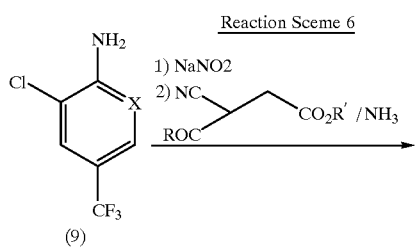
R: alkyl, alkoxy
R': alkyl
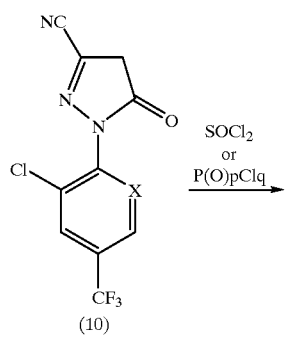
p = 0, 1
q = 3, 5
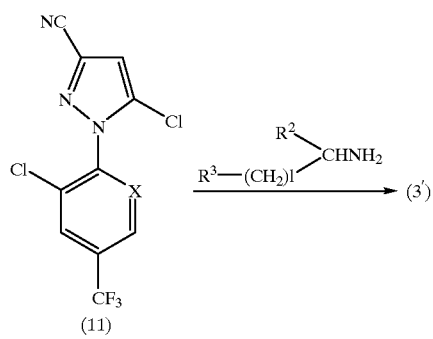
Reaction Scheme 8
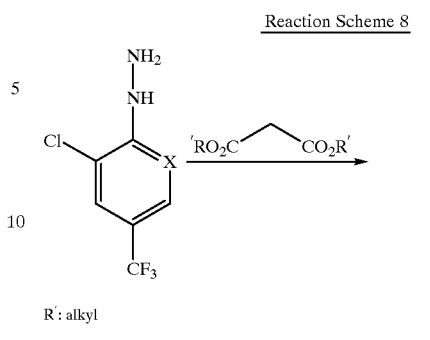
R': alkyl
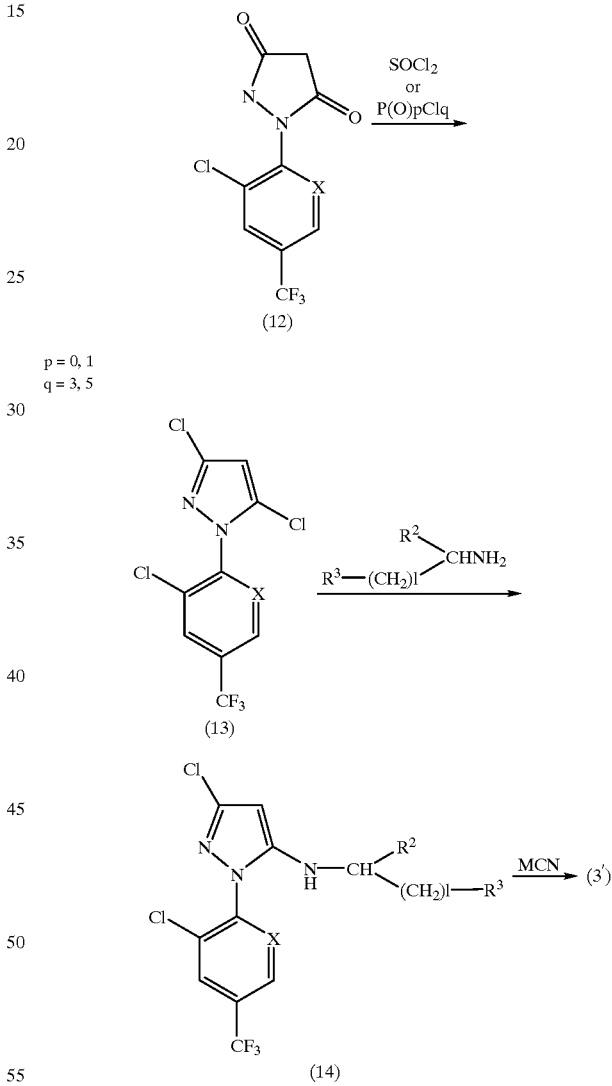
M = Li, Na, K, Cs
The process of reaction scheme 2 is characterized in that the compound of the general formula (5) is reduced with a reducing agent.

The reaction is carried out by adding 0.2 to 5.0 molar equivalents, preferably 0.25 to 2.0 molar equivalents of a reducing agent to the compound of the general formula (5) in the presence or absence of a solvent and allowing them to react at −20° to 150° C., preferably 0° to 120° C.

The reducing agent used for the reaction includes sodium borohydride, sodium cyanoborohydride, lithium borohydride, and lithium aluminum hydride.

The solvent used includes polar solvents such as ethers, e.g., diethyl ether, dioxane, and tetrahydrofuran, and alcohols, e.g., methanol, ethanol, and propanol.

The compound represented by the general formula (5) can be prepared by, for example, in accordance with the process described in an unexamined published Japanese patent application 5-148240.

The process of reaction scheme 3 is characterized in that the compound of the general formula (6) is (het) arylalkylated. In the scheme Z represents a releasable group such as a halogen atom and a hydroxyl group.

The reaction is carried out by allowing the compound (6) or an alkali metal derivative thereof and $R^3R^2CHZ$ (wherein $R^2$, $R^3$, and Z are as defined above) to react in a solvent in the presence of, if desired, a base at 0° to 150° C. The solvent useful in this reaction includes aromatic hydrocarbons such as benzene, toluene and xylene; ketones such as acetone and methyl ethyl ketone; halogenated hydrocarbons such as chloroform and methylene chloride; tetrahydrofuran, and N,N-dimethylformamide.

The base used in the reaction includes organic bases such as pyridine and triethylamine and alkali metal carbonates.

The compounds represented by the general formula (1) according to the present invention are useful in agriculture, horticulture and in the fields relating to housekeeping, cattle, and pets as controlling agents on pests such as arthropods (especially mites and insects), nematodes, worms and protozoa. Specifically the compounds have high controlling activities on eggs and larvae of Hemiptera, such as Delphacidae (e.g., *Sogatella furcifera, Nilaparvata lugens*, and *Laodelphax striatellus*), Deltocephalidae (e.g., *Nephotettix cincticeps* and *Tettigella viridis*), and Aphididae (e.g., *Myzus persicae*); Lepidoptera, such as *Spodoptera litura, Chilo suppressalis, Cuapha locrocis medinalis*, and *Plutella xylostella*; Coleoptera, such as *Callosobruchus chinensis*; Diptera, such as *Musca domestica, Aedes aegypti*, and *Culex pipiens pallens*; and Orthoptera, and are therefore useful as an active ingredient of agricultural and horticultural insecticides. The insects which are controllable by the compounds of the present invention are not limited to these examples.

In using the compounds of the invention as agricultural and horticultural insecticides, they may be used alone but are preferably formulated into compositions together with adjuvants customarily employed in the art. While not limiting, the forms of the agricultural and horticultural insecticides include emulsifiable concentrates, wettable powders, dusts, flowables, powders, granules, tablets, oils, sprays, and fumigants. These preparations can comprise one or more than one compounds of the invention as an active ingredient(s).

The adjuvants are used in the agricultural and horticultural insecticidal preparations for the purpose of improvement of the insecticidal effect, stabilization of the preparations, improvement of dispersibility, and the like. Useful adjuvants include carriers (diluents), spreaders, emulsifiers, wetting agents, dispersants, and disintegrants. Suitable liquid carriers include water; aromatic hydrocarbons such as toluene and xylene; alcohols such as methanol, butanol and glycol; ketones such as acetone; amides such as dimethylformamide; sulfoxides such as dimethyl sulfoxide; methylnaphthalene; cyclohexane; animal or vegetable oils; and fatty acids. Examples of suitable solid carriers are clay, kaolin, talc, diatomaceous earth, silica, calcium carbonate, montmorillonite, bentonite, feldspar, quartz, alumina, sawdust, nitrocellulose, starch, and gum arabic. General surface active agents serve as an emulsifier or a dispersant. For example, anionic, cationic, nonionic or amphoteric surface active agents, such as sodium higher alcohol sulfates, stearyltrimethylammonium chloride, polyoxyethylene alkylphenyl ethers, and lauryl betaine, are useful. Further, spreaders, such as polyoxyethylene nonylphenyl ether and polyoxyethylene laurylphenyl ether; wetting agents such as dialkyl sulfosuccinates; fixing agents, such as carboxymethyl cellulose and polyvinyl alcohol; and disintegrants, such as sodium lignin sulfonate and sodium laurylsulfate can be used.

The concentration of the active ingredient in the agricultural and horticultural insecticides is selected from the range of from 0.1 to 99.5%, being appropriately decided in accordance with various conditions such as the form of the preparation and the method of application. For example, a suitable active ingredient concentration is about 0.5 to 20% by weight, preferably 1 to 10% by weight, in dusts; about 1 to 90% by weight, preferably 10 to 80% by weight, in wettable powders; or about 1 to 90% by weight, preferably 10 to 40% by weight, in emulsifiable concentrates.

Emulsifiable concentrates are prepared by mixing the compound of the invention as an active ingredient with a solvent, a surface active agent, etc. The emulsifiable concentrate is diluted to a prescribed concentration on use. Wettable powders are prepared by mixing the active ingredient with a solid carrier, a surface active agent, etc. The wettable powder can be applied as diluted to a prescribed concentration. Dusts are prepared by mixing the active ingredient with a solid carrier, etc. and can be applied as such. Granules are prepared by mixing the active ingredient with a solid carrier, a surface active agent, etc., followed by granulation. Granules can be applied as such. The above description about the methods for preparing the above-described compositions of various forms is not intended to limit the invention, and one skilled in the art can select an appropriate method in accordance with the active ingredient and the purpose of application.

The agricultural and horticultural insecticide of the invention comprising the compound of the invention as an active ingredient can further contain optional active ingredients, such as other bactericides, insecticides, miticides, herbicides, insect growth regulators, fertilizers, soil conditioners, and so on.

The usage of the agricultural and horticultural insecticide according to the invention is not particularly restricted, and it can be used for foliar spray treatment, submerged application, pre-emergence soil treatment, seed treatment, and the like.

For foliar spray treatment, a solution having a concentration of 5 to 1000 ppm, preferably 10 to 500 ppm, is applied in an amount of about 100 to 200 l per 10 are. For submerged application, granules having an active ingredient content of 5 to 15% is scattered in an amount of 1 to 10 kg per 10 are. For soil treatment, a solution having a concentration of 5 to 1000 ppm is applied in an amount of about 1 to 10 l per $m^2$. For seed treatment, a solution having a concentration of 10 to 1000 ppm is applied in an amount of about 10 to 100 ml per kg of seeds.

The usage of the insecticide for cattle or pets according to the invention is not particularly restricted. The preparation can be applied in any manner, for example, by applying to a pet's collar or dusting cattle.

The present invention will now be illustrated in greater detail with reference to Examples, but it should be understood that the present invention is not limited thereto.

EXAMPLE 1

Preparation of 1-(2,6-Dichloro-4-trifluoromethylphenyl)-3-cyano-5-(4-pyridylmethylamino)pyrazole p-Toluenesulfonic acid was added to a mixture of 2.0 g of 1-(2,6-dichloro-4-trifluoromethylphenyl)-3-cyano-5-aminopyrazole, 0.7 g of pyridine-4-aldehyde, and 50 ml of toluene, and the mixture was heated under reflux for 5 hours. Any insoluble matter was removed, and the solvent was evaporated under reduced pressure. The residue was washed with hexane and a small amount of chloroform to give 2.0 g of crude 1-(2,6-dichloro-4-trifluoromethylphenyl)-3-cyano-5-(4-pyridylmethylideneimino)pyrazole.

Melting point: 194–195° C. $^1$H-NMR (CDCl$_3$): 6.87 (1H, s), 7.57 (2H, d), 7.79 (2H, s), 8.69 (1H, s), 8.76 (2H, d).

To a solution of 1.7 g of 1-(2,6-dichloro-4-trifluoromethylphenyl)-3-cyano-5-(4-pyridylmethylideneimino)pyrazole in 20 ml of methanol was added slowly 0.3 g of sodium borohydride, followed by stirring at room temperature for 1 hour. After ice was added to the reaction mixture, concentrated hydrochloric acid was slowly added thereto to neutralize. Ethyl acetate was added to the mixture to extract. The organic layer was washed with a saturated aqueous solution of sodium chloride and dried over anhydrous sodium sulfate. The residue was purified by silica gel column chromatography to give 1.5 g of 1-(2,6-dichloro-4-trifluoromethylphenyl)-3-cyano-5-(4-pyridylmethylamino)pyrazole.

Melting point: >300° C. $^1$H-NMR (CDCl$_3$): 3.98 (1H, t), 4.37 (2H, d), 5.80 (1H, s), 7.22 (2H, d), 7.80 (2H, s), 8.59 (2H, d).

EXAMPLE 2

Preparation of 1-(2,6-Dichloro-4-trifluoromethylphenyl)-3-cyano-4-trifluoromethylsulfenyl-5-(4-pyridylmethylamino) pyrazole (Compound No. 1)

In 10 ml of dichloromethane was suspended 0.5 g of 1-(2,6-dichloro-4-trifluoromethylphenyl)-3-cyano-5-(4-pyridylmethylamino)pyrazole obtained in Example 1 above, and 0.2 g of trifluoromethylsulfenyl chloride in 10 ml of dichloromethane was added thereto dropwise at −20° C. The mixture was taken out of the cooling bath. After stirring for 3 hours, ice-water was added to the mixture to extract. The organic layer was washed with a saturated sodium chloride aqueous solution and dried over anhydrous sodium sulfate. The residue was purified by silica gel column chromatography to yield 0.4 g of compound No. 1 shown in Table 1 below. The NMR data of the compound were as follows.

$^1$H-NMR (CDCl$_3$): 4.51 (2H, d), 4.65 (1H, b), 7.05 (2H, d), 7.70 (2H, s), 8.53 (2H, d).

EXAMPLE 3

Preparation of 1-(2,6-Dichloro-4-trifluoromethylphenyl)-3-cyano-4-trifluoromethylsulfenyl-5-(4-pyridylmethylamino) pyrazole (Compound No. 1)

To a solution of 2.6 g of 1-(2,6-dichloro-4-trifluoromethylphenyl)-3-cyano-4-trifluoromethylsulfenyl-5-(4-pyridylmethylideneimino)pyrazole in 15 ml of methanol was slowly added 0.37 g of sodium borohydride. After stirring at room temperature for 3 hours, ice was added to the reaction mixture, and concentrated hydrochloric acid was added thereto slowly to neutralize. Ethyl acetate was added to conduct extraction. The organic layer was washed with a saturated sodium chloride aqueous solution and dried over anhydrous sodium sulfate. The residue was purified by silica gel column chromatography to afford 1.2 g of compound No. 1 shown in Table 1.

EXAMPLE 4

Preparation of 1-(2,6-Dichloro-4-trifluoromethylphenyl)-3-cyano-4-trifluoromethylsulfenyl-5-[(3-methoxy-4-hydroxyphenyl)methylamino]pyrazole (Compound No. 2)

To a solution of 2.8 g of 1-(2,6-dichloro-4-trifluoromethylphenyl)-3-cyano-4-trifluoromethylsulfenyl-5-[(3-methoxy-4-hydroxyphenyl)methylideneimino]pyrazole in 15 ml of methanol was slowly added 0.37 g of sodium borohydride. After stirring at room temperature for 3 hours, ice was added to the reaction mixture, and concentrated hydrochloric acid was added thereto slowly to neutralize. Ethyl acetate was added to conduct extraction. The organic layer was washed with a saturated sodium chloride aqueous solution and dried over anhydrous sodium sulfate. The residue was purified by silica gel column chromatography to give 1.4 g of compound No. 2 shown in Table 1. The NMR data of the compound were as follows.

$^1$H-NMR (CDCl$_3$): 3.87 (3H, s), 4.32 (2H, m), 4.43 (1H, b), 5.60 (1H, bs), 6.62 (2H, m), 6.83 (1H, m), 7.73 (2H, s).

EXAMPLE 5

The compounds shown in Table 1 were obtained in the same manner as in Examples 2 to 4.

No. 3:
$^1$H-NMR (CDCl$_3$): 4.42 (2H, d), 4.54 (1H, bt), 7.12 (2H, m), 7.29 (3H, m), 7.68 (2H, s).

No. 4:
$^1$H-NMR (CDCl$_3$): 2.32 (3H, s), 4.36 (2H, d), 4.47 (1H, t), 7.01 (2H, d), 7.10 (2H, d), 7.67 (2H, s).

No. 5:
$^1$H-NMR (CDCl$_3$): 1.30 (9H, s), 4.38 (2H, d), 4.50 (1H, m), 7.05 (2H, d), 7.32 (2H, d), 7.69 (2H, s).

No. 6:
$^1$H-NMR (CDCl$_3$): 4.31 (2H, d), 4.38 (1H, m), 4.83 (1H, s), 6.75 (2H, d), 7.01 (2H, d), 7.71 (2H, s).

No. 7:
$^1$H-NMR (CDCl$_3$): 3.79 (3H, s), 4.34 (2H, d), 4.43 (1H, m), 6.82 (2H, d), 7.05 (2H, d), 7.70 (2H, s).

No. 8:
$^1$H-NMR (CDCl$_3$): 1.32 (6H, d), 4.32 (2H, d), 4.40 (1H, m), 4.51 (1H, m), 6.80 (2H, d), 7.02 (2H, d), 7.71 (1H, s).

No. 9:
$^1$H-NMR (CDCl$_3$): 4.39 (2H, d), 4.45 (1H, b), 6.9–7.4 (9H, m), 7.73 (2H, s).

No. 10:
$^1$H-NMR (CDCl$_3$): 4.42 (2H, d), 4.48 (1H, m), 7.01 (4H, q), 7.15 (2H, d), 7.60 (2H, d), 7.73 (2H, s).

No. 11:
$^1$H-NMR (CDCl$_3$): 4.43 (2H, d), 4.50 (1H, bt), 6.25 6.48 6.76 (1H, t), 7.05 (2H, d), 7.12 (2H, d), 7.70 (2H, s).

No. 12:
$^1$H-NMR (CDCl$_3$): 4.44 (2H, d), 4.57 (1H, t), 7.15 (4H, s), 7.69 (2H, s).

No. 13:
¹H-NMR (CDCl₃): 4.35 (4H, m), 4.46 (1H, m), 6.87 (2H, d), 7.09 (2H, d), 7.61 (2H, s).
No. 14:
¹H-NMR (CDCl₃): 4.39 (2H, d), 4.49 (1H, t), 6.98 (2H, t), 7.10 (2H, m), 7.70 (2H, s).
No. 15:
¹H-NMR (CDCl₃): 4.41 (2H, d), 4.52 (1H, b), 7.06 (2H, d), 7.27 (2H, d), 7.69 (2H, s).
No. 16:
¹H-NMR (CDCl₃): (4.40, 2H, d), (4.54, 1H, m), (7.00, 2H, d), (7.42, 2H, d), (7.69, 2H, s).
No. 17:
¹H-NMR (CDCl₃): 4.47 (2H, d), 4.54 (1H, m), 6.98 (1H, t), 7.09 (1H, t), 7.19 (1H, d), 7.27 (1H, m), 7.69 (2H, s).
No. 18:
¹H-NMR (CDCl₃): 4.49 (2H, d), 7.72 (1H, t), 7.23 (4H, m), 7.65 (2H, s).
No. 19:
¹H-NMR (CDCl₃): 4.52 (2H, d), 4.68 (1H, t), 7.24 (2H, d), 7.55 (2H, d), 7.66 (2H, s).
No. 20:
¹H-NMR (CDCl₃): 2.46 (3H, s), 4.37 (2H, d), 4.46 (1H, t), 7.04 (2H, d), 7.17 (2H, d), 7.70 (2H, s).
No. 21:
¹H-NMR (CDCl₃): 3.05 (3H, s), 4.71 (2H, d), 6.19 (1H, t), 7.41 2H, d), 7.74 (2H, s), 7.88 (2H, d).
No. 22:
¹H-NMR (CDCl₃): 1.32 (6H, d), 4.32 (2H, d), 4.40 (1H, m), 4.51 (1H, m), 6.80 (2H, d), 7.02 (2H, d), 7.71 (1H, s).
No. 23:
¹H-NMR (CDCl₃): 4.64 (3H, m), 7.33 (2H, d), 7.70 (2H, s), 8.16 (2H, d).
No. 24:
¹H-NMR (CDCl₃): 4.77 (2H<d), 5.01 (1H, m), 7.46 (2H, m), 7.61 (1H, m), 7.66 (2H, s), 8.01 (1H, d).
No. 25:
¹H-NMR (CDCl₃): 4.64 (2H, d), 6.35 (1H, t), 7.43 (2H, d), 7.54 (2H, m), 7.73 (2H, s).
No. 26:
¹H-NMR (CDCl₃): 1.44 (3H, t), 4.04 (2H, q), 4.30 (2H, d), 4.42 (1H, b), 5.65 (1H, s), 6.60 (2H, d), 6.82 (2H, d), 7.71 (2H, s).
No. 27:
¹H-NMR (CDCl₃): 4.47 (2H, d), 4.67 (1H, t), 7.21 (2H, s), 7.31 (1H, s), 7.68 (2H, s).
No. 28:
¹H-NMR (CDCl₃): 4.43 (2H, d), 4.63 (1H, b), 6.98 (2H, d), 7.25 (1H, d), 7.70 (2H, s).
No. 29:
¹H-NMR (CDCl₃): 4.49 (2H, d), 4.60 (1H, m), 6.95 (3H, m), 7.72 (2H, s).
No. 30:
¹H-NMR (CDCl₃): 4.66 (2H, d), 6.48 (1H, m), 7.37 (1H, dd), 7.49 (1H, d), 7.74 (2H, s), 7.76 (1H, d).
No. 31:
¹H-NMR (CDCl₃): 4.31 (2H, d), 4.42 (1H, t), 5.95 (2H, s), 6.59 (2H, m), 6.71 (1H, d), 7.72 (2H, s).
No. 32:
¹H-NMR (CDCl₃): 4.59 (2H, d), 4.63 (1H, m), 7.19 (1H, d), 7.49 (2H, m), 7.60 (3H, d), 7.77 (3H, m).
No. 33:
¹H-NMR (CDCl₃): 4.05 (3H, s+b), 7.22 (1H, m), 7.48 (1H, d), 7.72 (2H, s), 8.42 (1H, d), 8.53 (1H, d).
No. 34:
¹H-NMR (CDCl₃): 4.60 (2H, d), 6.11 (1H, b), 7.20 (2H, m), 7.67 (1H, t), 7.79 (2H, s), 8.40 (1H, d).
No. 35:
¹H-NMR (CDCl₃): 4.65 (2H, d), 5.74 (1H, t), 7.03 (2H, d), 7.74 (2H, d), 7.77 (2H, s).
No. 36:
¹H-NMR (CDCl₃): 4.54 (2H, d), 4.71 (1H, m), 6.98 (1H, d), 7.11 (1H, s), 7.73 (2H, s), 8.29 (2H, d).
No. 37:
¹H-NMR (CDCl₃): 4.45 (1H, b), 4.53 (2H, d), 7.28 (1H, d), 7.47 (1H, dd), 7.74 (2H, s), 8.20 (1H, d).
No. 38:
¹H-NMR (CDCl₃): 3.87 (3H, s), 4.4–4.6 (3H, m), 7.11 (1H, s), 7.25 (1H, d), 7.40 (2H, m), 8.17 (1H, d).
No. 39:
¹H-NMR (CDCl₃): 2.33 (3H, s), 4.58 (2H, d), 6.45 (1H, m), 6.99 (1H, d), 7.05 (1H, d), 7.56 (1H, t), 7.81 (2H, s).
No. 40:
¹H-NMR (CDCl₃): 4.623 (2H, d), 6.50 (1H, m), 7.12 (2H, s), 7.77 (2H, s).
No. 41:
¹H-NMR (CDCl₃): 4.74 (2H, d), 6.09 (1H, m), 7.84 (2H, s), 7.96 (1H, s), 8.65 (1H, s).
No. 42:
¹H-NMR (CDCl₃): 4.44 (3H, s), 6.17 (1H, d), 6.29 (1H, d), 7.31 (1H, d), 7.78 (2H, s).
No. 43:
¹H-NMR (CDCl₃): 4.28 (1H, bm), 4.29 (2H, d), 6.22 (1H, d), 7.30 (1H, s), 7.37 (1H, d), 7.77 (2H, s).
No. 44:
¹H-NMR (CDCl₃): 2.21 (3H, s), 4.36 (3H, bs), 5.87 (1H, s), 6.04 (1H, d), 7.78 (2H, s).
No. 45:
¹H-NMR (CDCl₃): 4.36 (1H, m), 4.44 (2H, d), 6.17 (1H, d), 6.22 (1H, d), 7.80 (2H, s).
No. 46:
¹H-NMR (CDCl₃): 4.38 (1H, b), 4.45 (2H, d), 6.23 (1H, s), 7.31 (1H, s), 7.79 (2H, s).
No. 47:
¹H-NMR (CDCl₃): 4.58 (1H, m), 4.66 (2H, d), 6.47 (1H, d), 7.22 (1H, d), 7.82 (2H, s).
No. 48:
¹H-NMR (CDCl₃): 4.42 (1H, m), 4.63 (2H, d), 6.88 (1H, d), 6.93 (1H, t), 7.24 (1H, m), 7.75 (2H, s).
No. 49:
¹H-NMR (CDCl₃): 4.44 (3H, b), 6.83 (1H, d), 7.07 (1H, m), 7.28 (1H, dd), 7.73 (2H, s).
No. 50:
¹H-NMR (CDCl₃): 2.43 (3H, s), 4.35 (1H, m), 4.52 (2H, d), 6.55 (1H, d), 6.65 (1H, d), 7.76(2H, s).
No. 51:
¹H-NMR (CDCl₃): 3.84 (3H, s), 4.29 (1H, m), 4.45 (2H, d), 5.17 (1H, d), 6.50 (1H, d), 7.77 (2H, s).
No. 52:
¹H-NMR (CDCl₃): 4.38 (1H, t), 4.57 (2H, d), 6.64 (1H, d), 6.87 (1H, d), 7.77 (2H, s).
No. 53:
¹H-NMR (CDCl₃): 4.54 (1H, t), 4.73 (2H, d), 6.85 (1H, d), 7.76 (1H, d), 7.79 (2H, s).
No. 54:
¹H-NMR (CDCl₃): 4.83 (2H, d), 5.17 (1H, t), 7.30 (1H, d), 7.66 (1H, d), 7.76 (2H, s).
No. 55:
¹H-NMR (CDCl₃): 2.27 (3H, s), 2.61 (3H, s), 4.59 (2H, d), 4.97 (1H, b), 7.78 (2H, s).
No. 56:
¹H-NMR (CDCl₃): 1.53 (3H, m), 4.28 (1H, t), 4.54 (2H, d), 5.52 (1H, m), 6.91 (1H, s), 7.79 (2H, s).
No. 57:

No. 57 (continued):
¹H-NMR (CDCl₃): 3.51 (3H, s), 4.01 (1H, t), 4.47 (2H, d), 6.05 (2H, m), 6.63 (1H, t), 7.78 (2H, s).
No. 58:
¹H-NMR (CDCl₃): 1.19 (3H, t), 2.57 (2H, q), 3.68 (3H, s), 4.09 (1H, m), 4.50 (2H, d), 5.94 (1H, s), 7.80 (2H, s).
No. 59:
¹H-NMR (CDCl₃): 4.34 (1H, t), 4.58 (2H, d), 7.12 (2H, m), 7.22 (1H, d), 7.38 (2H, m), 7.66 (2H, s), 8.14 (1H, b).
No. 60:
¹H-NMR (CDCl₃): 3.75 (3H, s), 4.33 (1H, m), 4.56 (2H, d), 6.96 (1H, s), 7.12 (1H, t), 7.26 (2H, m), 7.37 (1H, d), 7.65 (2H, s).
No. 61:
¹H-NMR (CDCl₃): 3.81 (3H, s), 4.30 (1H, t), 4.56 (2H, d), 6.84 (1H, s), 6.89 (1H, dd), 7.09 (1H, d), 7.27 (1H, d), 7.69 (2H, s), 8.03 (1H, b).
No. 62:
¹H-NMR (CDCl₃): 4.11 (2H, m), 6.45 (1H, b), 6.48 (1H, t), 6.98 (4H, q), 7.58 (1H, s), 7.63 (1H, s).
No. 63:
¹H-NMR (CDCl₃): 4.61 (2H, m), 6.58 (1H, t), 7.4–7.65 (5H, m), 7.94 (1H, d).
No. 64:
¹H-NMR (CDCl₃): 3.83 (3H, s), 4.01 (2H, d), 5.58 (1H, s), 6.30 (1H, m), 6.40 (1H, d), 6.55 (1H, s), 6.75 (1H, d), 7.63 (1H, s), 7.68 (1H, s).
No. 65:
¹H-NMR (CDCl₃): 4.17 (2H, d), 6.62 (1H, m), 6.89 (2H, d), 7.54 (1H, s), 7.61 (1H, s), 8.47 (2H, d).
No. 66:
¹H-NMR (CDCl₃): 4.16 (2H, d), 6.41 (1H, m), 7.19 (1H, m), 7.38 (1H, d), 7.61 (1H, s), 7.67 (1H, s), 8.23 (1H, s), 8.52 (1H, d).
No. 67:
¹H-NMR (CDCl₃): 4.34 (2H, d), 7.00 (1H, b), 7.17 (2H, m), 7.65 (1H, m), 7.71 (1H, s), 7.74 (1H, s), 8.38 (1H, d).
No. 68:
¹H-NMR (CDCl₃): 4.30 (2H, d), 6.21 (1H, t), 6.74 (1H, d), 6.88 (1H, t), 7.21 (1H, d), 7.70 (2H, d).
No. 69:
¹H-NMR (CDCl₃): 4.49 (2H, d), 4.73 (1H, t), 7.04 (2H, d), 7.69 (2H, s), 8.51 (2H, m).
No. 70:
¹H-NMR (CDCl₃): 4.50 (2H, d), 4.73 (1H, m), 7.04 (2H, d), 7.69 (2H, s), 8.52 (2H, d).
No. 71:
¹H-NMR (CDCl₃): 4.50 (2H, d), 4.75 (1H, t), 7.04 (2H, d), 7.69 (2H, s), 8.52 (2H, d).
No. 72:
¹H-NMR (CDCl₃): 2.25 (3H, s), 4.31 (1H, b), 4.37 (2H, d), 7.14 (2H, m), 7.29 (3H, m), 7.67 (2H, s).
No. 73:
¹H-NMR (CDCl₃): 2.24 (3H, s), 4.40 (1H, m), 4.51 (2H, d), 7.10 (2H, d), 7.70 (2H, s), 8.52 (2H, d).
No. 74:
¹H-NMR (CDCl₃): 1.24 (3H, t), 2.66 (2H, q), 4.45 (2H, d), 4.54 (1H, t), 7.06 (2H, d), 7.66 (2H, s), 8.49 (2H, d).
No. 75:
¹H-NMR (CDCl₃): 1.28 (6H, d), 3.13 (1H, m), 4.39 (2H, d), 4.64 (1H, t), 7.04 (2H, d), 7.64 (2H, s), 8.47 (2H, d).
No. 76:
¹H-NMR (CDCl₃): 3.87 (3H, s), 4.24 (2H, s), 6.87 (2H, d), 7.73 (2H, s), 8.48 (2H, d).
No. 77:
¹H-NMR (CDCl₃): 2.25 (3H, s), 4.17 (1H, d), 5.16 (1H, d), 6.72 (2H, d), 7.26 (1H, s), 7.71 (1H, s), 8.33 (2H, d).
No. 78:
¹H-NMR (CDCl₃): 4.61 (2H, d), 4.67 (1H, m), 7.49 (2H, m), 7.70 (2H, s), 8.00 (1H, s), 8.13 (1H, m).

TABLE 1

| Compound No. | S(O)nR¹ | R³ | R⁴ | m.p. (° C.) |
|---|---|---|---|---|
| 1 | SCF₃ | 4-pyridyl | H | 148–150 |
| 2 | SCF₃ | 3-methoxy-4-hydroxyphenyl | H | 143–145 |
| 3 | SCF₃ | phenyl | H | 152–154 |
| 4 | SCF₃ | 4-methylphenyl | H | 175 |
| 5 | SCF₃ | 4-tert-butylphenyl | H | 136–137 |

TABLE 1-continued

| Compound No. | S(O)nR¹ | R³ | R⁴ | m.p. (° C.) |
|---|---|---|---|---|
| 6 | SCF₃ | 4-HO-C₆H₄- | H | 180–182 |
| 7 | SCF₃ | 4-CH₃O-C₆H₄- | H | 124–126 |
| 8 | SCF₃ | 4-iC₃H₇O-C₆H₄- | H | 150–151 |
| 9 | SCF₃ | 4-(C₆H₅O)-C₆H₄- | H | 167–168 |
| 10 | SCF₃ | 4-(4-CF₃-C₆H₄-O)-C₆H₄- | H | 139–141 |
| 11 | SCF₃ | 4-CHF₂O-C₆H₄- | H | 122–124 |
| 12 | SCF₃ | 4-CF₃O-C₆H₄- | H | 141–143 |
| 13 | SCF₃ | 4-CF₃CH₂O-C₆H₄- | H | 153–154 |
| 14 | SCF₃ | 4-F-C₆H₄- | H | 164 |
| 15 | SCF₃ | 4-Cl-C₆H₄- | H | 158–160 |
| 16 | SCF₃ | 4-Br-C₆H₄- | H | 157–159 |
| 17 | SCF₃ | 2-F-C₆H₄- | H | 140–141 |
| 18 | SCF₃ | 2-Cl-C₆H₄- | H | 168–169 |

TABLE 1-continued

| Compound No. | S(O)nR¹ | R³ | R⁴ | m.p. (° C.) |
|---|---|---|---|---|
| 19 | SCF₃ | 4-CF₃-C₆H₄ | H | 158–159 |
| 20 | SCF₃ | 4-SCH₃-C₆H₄ | H | 157–159 |
| 21 | SCF₃ | 4-SO₂CH₃-C₆H₄ | H | 216–217 |
| 22 | SCF₃ | 4-CN-C₆H₄ | H | 174–175 |
| 23 | SCF₃ | 4-NO₂-C₆H₄ | H | 169–171 |
| 24 | SCF₃ | 2-NO₂-C₆H₄ | H | 157–158 |
| 25 | SCF₃ | 3-CN-C₆H₄ | H | 226–228 |
| 26 | SCF₃ | 3-OC₂H₅-4-OH-C₆H₃ | H | 125–127 |
| 27 | SCF₃ | 2,4-Cl₂-C₆H₃ | H | 197–198 |
| 28 | SCF₃ | 3,5-Cl₂-C₆H₃ | H | 174–176 |
| 29 | SCF₃ | 2,5-F₂-C₆H₃ | H | 156–158 |

TABLE 1-continued
| Compound No. | S(O)nR¹ | R³ | R⁴ | m.p. (° C.) |
|---|---|---|---|---|
| 30 | SCF₃ | 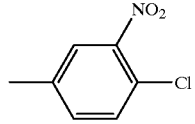 | H | 236–237 |
| 31 | SCF₃ | 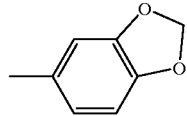 | H | 141–143 |
| 32 | SCF₃ | 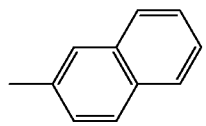 | H | 159–160 |
| 33 | SCF₃ | 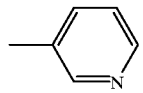 | H | 148–149 |
| 34 | SCF₃ | 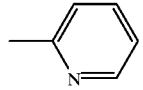 | H | 131–133 |
| 35 | SCF₃ | 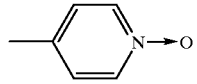 | H | 191–193 |
| 36 | SCF₃ | 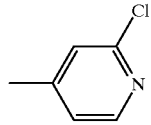 | H | 181–182 |
| 37 | SCF₃ | 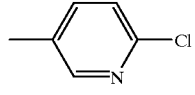 | H | 129–131 |
| 38 | SCF₃ | 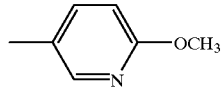 | H | 143–145 |
| 39 | SCF₃ | 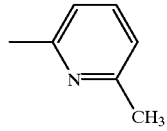 | H | 117–119 |
| 40 | SCF₃ | 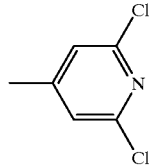 | H | 216–218 |

TABLE 1-continued

| Compound No. | S(O)nR¹ | R³ | R⁴ | m.p. (° C.) |
|---|---|---|---|---|
| 41 | SCF₃ | 3-chloro-2-methyl-5-(trifluoromethyl)pyridin-yl | H | 121–123 |
| 42 | SCF₃ | 5-methylfuran-2-yl | H | 144–145 |
| 43 | SCF₃ | 4-methylfuran-3-yl | H | 152–154 |
| 44 | SCF₃ | 2,5-dimethylfuran-yl | H | 131–133 |
| 45 | SCF₃ | 5-bromo-2-methylfuran-yl | H | 141–142 |
| 46 | SCF₃ | 3-bromo-4-methylfuran-yl | H | 157–159 |
| 47 | SCF₃ | 2-methyl-5-nitrofuran-yl | H | 154–156 |
| 48 | SCF₃ | 5-methylthiophen-2-yl | H | 171–172 |
| 49 | SCF₃ | 4-methylthiophen-3-yl | H | 169–171 |
| 50 | SCF₃ | 2,5-dimethylthiophen-yl | H | 173–175 |
| 51 | SCF₃ | 5-methoxy-2-methylthiophen-yl | H | 152–153 |
| 52 | SCF₃ | 5-bromo-2-methylthiophen-yl | H | 160–161 |
| 53 | SCF₃ | 2-methyl-5-nitrothiophen-yl | H | 177–179 |

TABLE 1-continued
| Compound No. | S(O)nR¹ | R³ | R⁴ | m.p. (° C.) |
|---|---|---|---|---|
| 54 | SCF₃ | 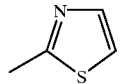 | H | 148–149 |
| 55 | SCF₃ | 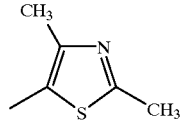 | H | 201–203 |
| 56 | SCF₃ | 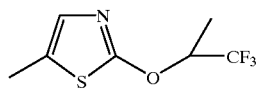 | H | 181–182 |
| 57 | SCF₃ | 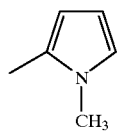 | H | 120–121 |
| 58 | SCF₃ | 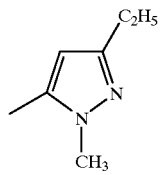 | H | 179–180 |
| 59 | SCF₃ | 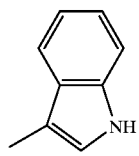 | H | 183–185 |
| 60 | SCF₃ | 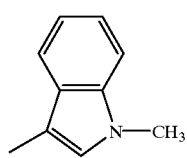 | H | 167–169 |
| 61 | SCF₃ | 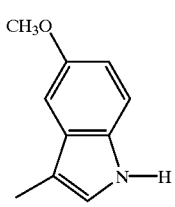 | H | 160–162 |
| 62 | S(O)CF₃ | 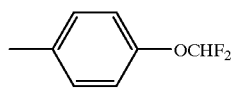 | H | 133–134 |
| 63 | S(O)CF₃ | 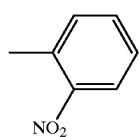 | H | 146–148 |

TABLE 1-continued
| Compound No. | S(O)nR¹ | R³ | R⁴ | m.p. (° C.) |
|---|---|---|---|---|
| 64 | S(O)CF₃ | 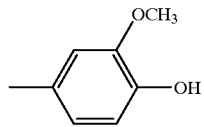 | H | 182–183 |
| 65 | S(O)CF₃ | 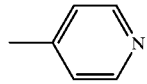 | H | 88–90 |
| 66 | S(O)CF₃ | 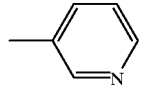 | H | 165–167 |
| 67 | S(O)CF₃ | 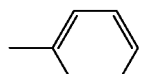 | H | 179–181 |
| 68 | S(O)CF₃ | 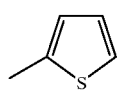 | H | 179–181 |
| 69 | SCF₂CF₃ | 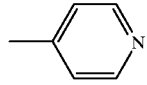 | H | 191–193 |
| 70 | SCF₂(CF₂)₂CF₃ | 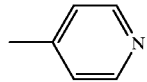 | H | 133–134 |
| 71 | SCF₂(CF₂)₆CF₃ | 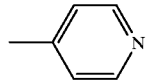 | H | 127–129 |
| 72 | SCH₃ | 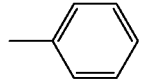 | H | 127–128 |
| 73 | SCH₃ | 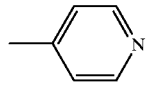 | H | 118–120 |
| 74 | SC₂H₅ | 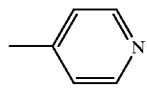 | H | 139–140 |
| 75 | SC₃H₇ | 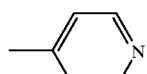 | H | 140–142 |
| 76 | SCF₃ | 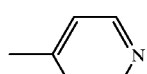 | CH₃ | 114–115 |

TABLE 1-continued

| Compound No. | S(O)nR¹ | R³ | R⁴ | m.p. (° C.) |
|---|---|---|---|---|
| 77 | SCF₃ | 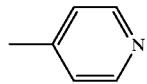 | COCH₃ | 184–186 |
| 78 | SCF₃ | 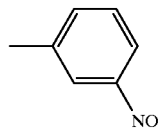 | H | 206–208 |

X = CCl, R² = H

Formulation Examples and Test Examples of the agricultural and horticultural insecticides containing the compound of the invention as an active ingredient are shown below for illustrative purposes only but not for limitation.

FORMULATION EXAMPLE 1
Wettable Powder:

Twenty parts by weight of the compound of the present invention, 20 parts by weight of Carplex #80 (a trade name of the white carbon produced by Shionogi & Co., Ltd.), 52 parts by weight of ST Kaolin Clay (a trade name of the kaolinite produced by Tsuchiya Kaolin K.K.), 5 parts by weight of Sorpol 9047K (a trade name of the anionic surface active agent produced by Toho Chemical Industry Co., Ltd.), and 3 parts by weight of Runox P65L (a trade name of the anionic surface active agent produced by Toho Chemical Industry Co., Ltd.) were mixed and ground uniformly to obtain a wettable powder containing 20% by weight of the active ingredient.

FORMULATION EXAMPLE 2
Dust:

Two parts by weight of the compound of the present invention, 93 parts by weight of clay (produced by Nippon Talc K.K.), and 5 parts by weight of Carplex #80 (a trade name of the white carbon produced by Shionogi & Co., Ltd.) were uniformly mixed and ground to obtain a dust containing 2% by weight of the active ingredient.

FORMULATION EXAMPLE 3
Emulsifiable Concentrate:

In a mixed solvent of 35 parts by weight of xylene and 30 parts by weight of dimethylformamide was dissolved 20 parts by weight of the compound of the present invention, and 15 parts by weight of Sorpol 3005X (a trade name of a mixture of a nonionic surface active agent and an anionic surface active agent, available from Toho Chemical Co., Ltd.) was added thereto to prepare an emulsifiable concentrate containing 20% by weight of the active ingredient.

FORMULATION EXAMPLE 4
Flowable:

A mixture of 30 parts by weight of the compound of the present invention, 5 parts by weight of Sorpol 9047K, 3 parts by weight of Sorbon T-20 (a trade name of the nonionic surface active agent produced by Toho Chemical Co., Ltd.), 8 parts by weight of ethylene glycol, and 44 parts by weight of water were wet ground in Dynomill (produced by Shinmaru enterprises Co.). To the resulting slurry was added 10 parts by weight of a 1 wt % aqueous solution of xanthan gum (naturally occurring polymer), followed by mixing and grinding thoroughly to obtain a flowable containing 20% by weight of the active ingredient.

TEST EXAMPLE 1
Insecticidal Effect on Larvae of *Nilaparvata lugens*:

A rice seedling was planted in a glass cylinder (inner diameter: 3 cm; length: 17 cm), and five 4th instar larvae of *Nilaparvata lugens* were set free therein. An agricultural and horticultural insecticide was prepared in accordance with Formulation Example 3 and diluted with water, and 0.5 ml of the resulting emulsion was sprayed in the cylinder by means of a spray tower (manufactured by Mizuho Rika) (duplicates at a concentration). The cylinder was kept in a thermostat at 25° C., and the mortality and agony of the larvae were examined after 5 days from the treatment to obtain a death rate (%) taking an agonizing insect as a ½ dead insect. The results obtained are shown in Table 2 (the compound numbers in Table 2 correspond to the numbers in Table 1).

TABLE 2

| Compound No. | Concentration (ppm) | Death Rate (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 8 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| 17 | 500 | 100 |
| 18 | 500 | 100 |
| 19 | 500 | 100 |
| 20 | 500 | 100 |
| 22 | 500 | 100 |
| 23 | 500 | 100 |
| 24 | 500 | 100 |
| 25 | 500 | 100 |
| 26 | 500 | 100 |
| 27 | 500 | 100 |
| 28 | 500 | 100 |
| 29 | 500 | 100 |
| 30 | 500 | 100 |
| 31 | 500 | 100 |
| 32 | 500 | 100 |

TABLE 2-continued

| Compound No. | Concentration (ppm) | Death Rate (%) |
|---|---|---|
| 33 | 500 | 100 |
| 34 | 500 | 100 |
| 35 | 500 | 100 |
| 36 | 500 | 100 |
| 37 | 500 | 100 |
| 39 | 500 | 100 |
| 40 | 500 | 100 |
| 41 | 500 | 100 |
| 42 | 500 | 100 |
| 43 | 500 | 100 |
| 44 | 500 | 100 |
| 45 | 500 | 100 |
| 46 | 500 | 100 |
| 47 | 500 | 100 |
| 48 | 500 | 100 |
| 49 | 500 | 100 |
| 50 | 500 | 100 |
| 51 | 500 | 100 |
| 52 | 500 | 100 |
| 54 | 500 | 100 |
| 57 | 500 | 100 |
| 58 | 500 | 100 |
| 59 | 500 | 100 |
| 60 | 500 | 100 |
| 62 | 500 | 100 |
| 64 | 500 | 100 |
| 65 | 500 | 100 |
| 66 | 500 | 100 |
| 67 | 500 | 100 |
| 69 | 500 | 100 |
| 73 | 500 | 100 |
| 74 | 500 | 100 |
| 75 | 500 | 100 |

TEST EXAMPLE 2

Insecticideal Effect on Larvae of *Plutella xylostella*:

A disc (6 cm in diameter) cut out of a cabbage leaf was soaked in an aqueous suspension of the agricultural and horticultural insecticide prepared in accordance with Formulation Example 1 for 1 minute, air-dried, and placed in a plastic cup (inner diameter: 7 cm). Five 3-instar larvae of *Plutella xylostella* were set free in the cup (duplicates at a concentration). The cup was kept in a thermostat at 25° C., and the death and agony of the larvae were examined after 4 days from the treatment to obtain a death rate (%) taking an agonizing insect as a ½ dead insect. The results obtained are shown in Table 3 (the compound numbers in the Table below correspond to the numbers in Table 1).

TABLE 3

| Compound No. | Concentration (ppm) | Death Rate (%) |
|---|---|---|
| 1 | 500 | 100 |
| 2 | 500 | 100 |
| 3 | 500 | 100 |
| 4 | 500 | 100 |
| 6 | 500 | 100 |
| 7 | 500 | 100 |
| 8 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| 17 | 500 | 100 |
| 18 | 500 | 100 |
| 19 | 500 | 100 |
| 20 | 500 | 100 |
| 21 | 500 | 100 |
| 22 | 500 | 100 |
| 23 | 500 | 100 |
| 24 | 500 | 100 |
| 25 | 500 | 100 |
| 26 | 500 | 100 |
| 27 | 500 | 100 |
| 28 | 500 | 100 |
| 29 | 500 | 100 |
| 30 | 500 | 100 |
| 31 | 500 | 100 |
| 32 | 500 | 100 |
| 33 | 500 | 100 |
| 34 | 500 | 100 |
| 35 | 500 | 100 |
| 36 | 500 | 100 |
| 37 | 500 | 100 |
| 39 | 500 | 100 |
| 40 | 500 | 100 |
| 41 | 500 | 100 |
| 42 | 500 | 100 |
| 43 | 500 | 100 |
| 44 | 500 | 100 |
| 45 | 500 | 100 |
| 46 | 500 | 100 |
| 47 | 500 | 100 |
| 48 | 500 | 100 |
| 49 | 500 | 100 |
| 50 | 500 | 100 |
| 51 | 500 | 100 |
| 52 | 500 | 100 |
| 54 | 500 | 100 |
| 57 | 500 | 100 |
| 58 | 500 | 100 |
| 59 | 500 | 100 |
| 60 | 500 | 100 |
| 62 | 500 | 100 |
| 64 | 500 | 100 |
| 65 | 500 | 100 |
| 66 | 500 | 100 |
| 67 | 500 | 100 |
| 69 | 500 | 100 |
| 70 | 500 | 100 |
| 73 | 500 | 100 |
| 74 | 500 | 100 |
| 75 | 500 | 100 |

TEST EXAMPLE 3

Insecticidal Effect on Larvae of *Spodoptera litura*:

A disc (6 cm in diameter) cut out of a cabbage leaf was soaked in an aqueous suspension of an agricultural and horticultural insecticide prepared in accordance with Formulation Example 1 for 1 minute, air-dried, and placed in a plastic cup (inner diameter: 7 cm). Five 3-instar larvae of *Spodoptera litura* were set free in the cup (duplicates at a concentation). The cup was kept in a thermostat at 25° C., and the death and agony of the larvae were examined after 5 days from the treatment to obtain a death rate (%) taking an agonizing insect as a ½ dead insect. The results obtained are show in Table 4 (the compound numbers in the Table below correspond to the numbers in Table 1).

TABLE 4

| Compound No. | Concentration (ppm) | Death Rate (%) |
|---|---|---|
| 1 | 500 | 100 |
| 2 | 500 | 100 |
| 3 | 500 | 100 |
| 7 | 500 | 100 |
| 11 | 500 | 100 |
| 15 | 500 | 100 |

TABLE 4-continued

| Compound No. | Concentration (ppm) | Death Rate (%) |
|---|---|---|
| 16 | 500 | 100 |
| 17 | 500 | 100 |
| 18 | 500 | 100 |
| 20 | 500 | 100 |
| 22 | 500 | 100 |
| 23 | 500 | 100 |
| 24 | 500 | 100 |
| 28 | 500 | 100 |
| 29 | 500 | 100 |
| 33 | 500 | 100 |
| 34 | 500 | 100 |
| 35 | 500 | 100 |
| 36 | 500 | 100 |
| 37 | 500 | 100 |
| 39 | 500 | 100 |
| 40 | 500 | 100 |
| 42 | 500 | 100 |
| 43 | 500 | 100 |
| 44 | 500 | 100 |
| 45 | 500 | 100 |
| 46 | 500 | 100 |
| 47 | 500 | 100 |
| 48 | 500 | 100 |
| 49 | 500 | 100 |
| 51 | 500 | 100 |
| 54 | 500 | 100 |
| 57 | 500 | 100 |
| 59 | 500 | 100 |
| 60 | 500 | 100 |
| 62 | 500 | 100 |
| 65 | 500 | 100 |
| 66 | 500 | 100 |
| 67 | 500 | 100 |
| 68 | 500 | 100 |
| 69 | 500 | 100 |

TEST EXAMPLE 4

Insecticidal Effect on Imagoes of *Callosobruchus chinensis:*

Two adzuki beans were put in a glass cylinder (inner diameter: 3 cm; length: 15 cm), and 10 imagoes of *Callosobruchus chinensis* were set free therein. An agricultural and horticultural insecticide was prepared in accordance with Formulation Example 3 and diluted with water, and 0.3 ml of the resulting emulsion was sprayed in the glass cylinder by means of a spray tower (manufactured by Mizuho Rica) (duplicates at a concentration). The cylinder was kept in a thermostat at 25° C., and the mortality and agony of the larvea were examined after 4 days from the treatment to obtain a death rate (%) taking an agonizing insect as a ½ dead insect. The results obtained are shown in Table 5 (the compound numbers in the Table correspond to the numbers in Table 1).

TABLE 5

| Compound No. | Concentration (ppm) | Death Rate (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 8 | 500 | 100 |
| 9 | 500 | 100 |
| 10 | 500 | 100 |
| 11 | 500 | 100 |
| 12 | 500 | 100 |
| 13 | 500 | 100 |

TABLE 5-continued

| Compound No. | Concentration (ppm) | Death Rate (%) |
|---|---|---|
| 14 | 500 | 100 |
| 15 | 500 | 100 |
| 16 | 500 | 100 |
| 17 | 500 | 100 |
| 18 | 500 | 100 |
| 19 | 500 | 100 |
| 20 | 500 | 100 |
| 21 | 500 | 100 |
| 22 | 500 | 100 |
| 23 | 500 | 100 |
| 24 | 500 | 100 |
| 25 | 500 | 100 |
| 26 | 500 | 100 |
| 27 | 500 | 100 |
| 28 | 500 | 100 |
| 29 | 500 | 100 |
| 30 | 500 | 100 |
| 31 | 500 | 100 |
| 32 | 500 | 100 |
| 33 | 500 | 100 |
| 34 | 500 | 100 |
| 35 | 500 | 100 |
| 36 | 500 | 100 |
| 37 | 500 | 100 |
| 39 | 500 | 100 |
| 40 | 500 | 100 |
| 41 | 500 | 100 |
| 42 | 500 | 100 |
| 43 | 500 | 100 |
| 44 | 500 | 100 |
| 45 | 500 | 100 |
| 46 | 500 | 100 |
| 47 | 500 | 100 |
| 48 | 500 | 100 |
| 49 | 500 | 100 |
| 50 | 500 | 100 |
| 51 | 500 | 100 |
| 52 | 500 | 100 |
| 54 | 500 | 100 |
| 57 | 500 | 100 |
| 58 | 500 | 100 |
| 59 | 500 | 100 |
| 60 | 500 | 100 |
| 62 | 500 | 100 |
| 64 | 500 | 100 |
| 65 | 500 | 100 |
| 66 | 500 | 100 |
| 67 | 500 | 100 |
| 69 | 500 | 100 |
| 73 | 500 | 100 |
| 74 | 500 | 100 |

TEST EXAMPLE 5

Insecticidal Effect on Larvae of *Myzus persicae:*

Water was put in a screw bottle (volume: 10 ml), and a leafstalk of Japanese radish was placed therein and inoculated with 5 to 6 imagoes of *Myzus persicae* per leave. After the inoculation, the bottle was put in a glass cylinder (diameter: 3.5 cm; height: 15 cm) with a mesh cover, and the insects were let to proliferate in a thermostat kept at 25° C. for 3 days. The imagoes on the leaves were removed, and the leaves were dipped in an aqueous emulsion of an agricultural and horticultural insecticide prepared according to Formulation Example 3 for about 5 seconds and then returned into the glass cylinder (duplicates at a concentration). The cylinder was maintained in the thermostat at 25° C., and the number of the insects on the leaves was counted on the 4th day after the treatment to obtain a death rate (%). The results obtained are shown in Table 6 (the compound numbers in the Table correspond to the numbers in Table 1).

TABLE 6

| Compound No. | Concentration (ppm) | Death Rate (%) |
|---|---|---|
| 1 | 500 | 100 |
| 2 | 500 | 100 |
| 11 | 500 | 100 |
| 24 | 500 | 100 |
| 42 | 500 | 100 |
| 47 | 500 | 100 |
| 57 | 500 | 100 |
| 65 | 500 | 100 |
| 73 | 500 | 100 |

TEST EXAMPLE 6

Low Concentration Test:

Effects on the larvae of *Plutella xylostella* of compound Nos. 2 and 57 of the invention and, for comparison, the compound I described in an unexamined published Japanese patent application 63-316771 and the compounds II and III described in an unexamined published Japanese patent application 5-148240 were examined at varied concentrations. The results obtained are shown in Table 7 (the compound numbers in the Table correspond to the numbers in Table 1).

TABLE 7

| Compound | Concentration (ppm) | Death Rate (%) | | |
|---|---|---|---|---|
| | | *Spodoptera litura* | *Plutella xylostella* | *Myzus persicae* |
| I | 200 | 100 | 100 | 50 |
| | 50 | 100 | 100 | 60 |
| | 12.5 | 50 | 100 | 50 |
| | 3.1 | 0 | 100 | 0 |
| | 0.8 | — | 85 | — |
| | 0.2 | — | 20 | — |
| | 0.05 | — | — | — |
| No. 1 | 200 | 100 | 100 | 100 |
| | 50 | 100 | 100 | 100 |
| | 12.5 | 100 | 100 | 98 |
| | 3.1 | 95 | 100 | — |
| | 0.8 | — | 100 | — |
| | 0.2 | — | 100 | — |
| | 0.05 | — | 95 | — |
| II | 200 | 100 | 100 | 0 |
| | 50 | 200 | 100 | — |
| | 12.5 | 95 | 100 | — |
| | 3.1 | 60 | 100 | — |
| | 0.8 | — | 100 | — |
| | 0.2 | — | 100 | — |
| | 0.05 | — | 80 | — |
| No. 57 | 200 | 100 | 100 | 100 |
| | 50 | 100 | 100 | 90 |
| | 12.5 | 70 | 100 | 80 |
| | 3.1 | — | 100 | — |
| | 0.8 | — | 100 | — |
| | 0.2 | — | 40 | — |
| | 0.05 | — | — | — |
| III | 200 | 100 | 100 | 0 |
| | 50 | 95 | 100 | — |
| | 12.5 | 65 | 100 | — |
| | 3.1 | — | 75 | — |
| | 0.8 | — | 20 | — |
| | 0.2 | — | — | — |
| | 0.05 | — | — | — |

I: Pyrazole compound with NC, SCF$_3$, NHC$_3$H$_7^n$ substituents and 2,6-dichloro-4-trifluoromethylphenyl group.

No. 1: Pyrazole compound with NC, SCF$_3$, NH-CH$_2$-(4-pyridyl) substituents and 2,6-dichloro-4-trifluoromethylphenyl group.

II: Pyrazole compound with NC, SCF$_3$, N=CH-(4-pyridyl) substituents and 2,6-dichloro-4-trifluoromethylphenyl group.

No. 57: Pyrazole compound with NC, SCF$_3$, NH-CH$_2$-(N-methylpyrrol-2-yl) substituents and 2,6-dichloro-4-trifluoromethylphenyl group.

III: Pyrazole compound with NC, SCF$_3$, N=CH-(N-methylpyrrol-2-yl) substituents and 2,6-dichloro-4-trifluoromethylphenyl group.

TEST EXAMPLE 7
Single Oral Dose Administration Test in Mice:

Acute toxicity (p.o.) compound No. 1 in mice was examined as follows. For comparison, compound IV disclosed in an unexamined published Japanese patent application 63-316771 was tested similarly.

Each test compound (300 mg) was suspended in 10 ml of a 0.5% CMC-Na aqueous solution. Five 6-week-old CD-1 male mice (available from Charles River) per group were forced to take an oral dose of 10 ml/kg of the suspension. The number of dead mice was counted after 7 days from the administration to obtain a death rate. The results obtained are shown in Table 8.

TABLE 8

| Compound | Dose (mg/kg) | Death Rate (%) |
|---|---|---|
| 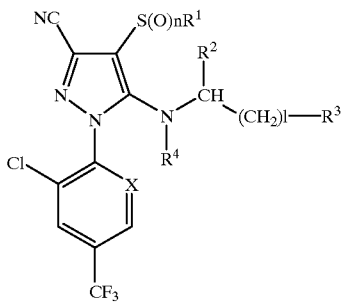 IV | 300 | 80 |
| No. 2 | 300 | 0 |

Industrial Applicability:

The 1-aryl-3-cyano-5-(het)arylalkylaminopyrazole derivatives of the present invention are characterized by excellent insecticidal effects, broad insecticidal spectra, high safety, and reduced adverse influences on the environment and are useful as novel pesticides.

What is claimed is:

1. A 1-aryl-3-cyano-5-(het)arylalkylaminopyrazole derivative represented by the general formula (1):

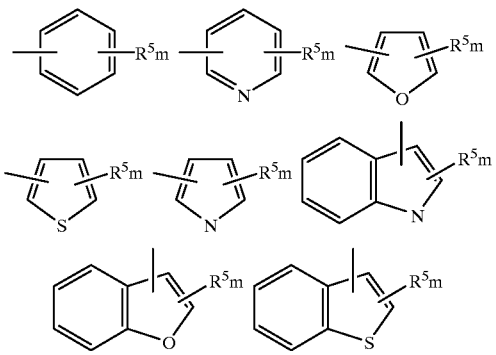

(1)

wherein $R^1$ represents a C1–C4 alkyl group or a C1–C8 haloalkyl group; $R^2$ represents a hydrogen atom or a C1–C4 alkyl group; $R^3$ represents an aryl or heteroaryl group which may be substituted with a substituent selected from a hydrogen atom, a hydroxyl group, a C1–C4 alkyl group, a C1–C8 haloalkyl group, a C1–C4 alkoxy group, a phenoxy group which may be substituted, a C1–C4 haloalkoxy group, a C1–C4 alkylthio group, a C1–C4 alkylsulfinyl group, a C1–C4 alkylsulfonyl group, a halogen atom, a nitro group, and a cyano group; and $R^4$ represents a hydrogen atom, a C1–C4 alkyl group or a C1–C5 acyl group; X represents a nitrogen atom or a halogen-substituted carbon atom; and l and n each independently represent 0, 1 or 2, provided that, when n=1, $R^3$ is not a phenyl group.

2. A 1-aryl-3-cyano-5-(het)arylalkylaminopyrazole derivative according to claim 1, wherein $R^2$ is a hydrogen atom.

3. A 1-aryl-3-cyano-5-(het)arylalkylaminopyrazole derivative according to claim 1, wherein $R^3$ is

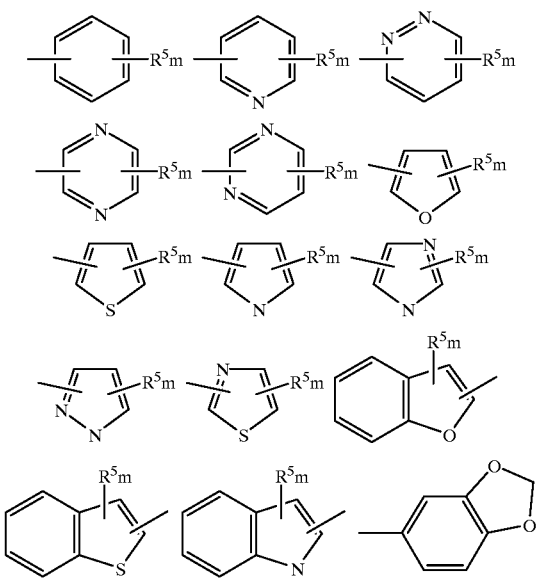

wherein $R^5$ represents a hydrogen atom, a hydroxyl group, a C1–C4 alkyl group, a C1–C8 haloalkyl group, a C1–C4 alkoxy group, a phenoxy group which may be substituted, a C1–C4 haloalkoxy group, a C1–C4 alkylthio group, a C1–C4 alkylsulfinyl group, a C1–C4 alkylsulfonyl group, a halogen atom, a nitro group, or a cyano group; and m represents 0, 1 or 2.

4. A 1-aryl-3-cyano-5-(het)arylalkylaminopyrazole derivative according to claim 1, wherein $R^3$ is wherein $R^5$ represents a hydrogen atom, a hydroxyl group, a C1–C4 alkyl group, a C1–C8 haloalkyl group, a C1–C4 alkoxy group, a phenoxy group which may be substituted, a C1–C4 haloalkoxy group, a C1–C4 alkylthio group, a C1–C4 alkylsulfinyl group, a C1–C4 alkylsulfonyl group, a halogen atom, a nitro group, or a cyano group; and m represents 0, 1 or 2.

5. A 1-aryl-3-cyano-5-(het)arylalkylaminopyrazole derivative according to claim 1, wherein R³ is

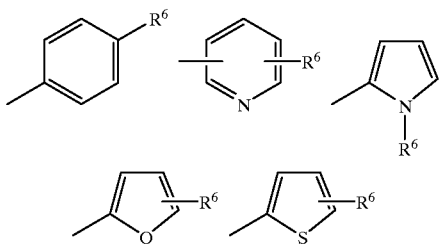

wherein R⁶ represents a hydrogen atom, a hydroxyl group, a C1–C2 alkyl group, a C1–C2 alkoxy group, a C1–C2 haloalkyl group, a C1–C2 alkylthio group, a halogen atom, a nitro group, or a cyano.

6. A 1-aryl-3-cyano-5-(het)arylalkylaminopyrazole derivative represented by the general formula (2):

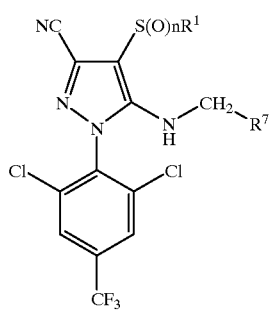

(2)

wherein R⁷ represents

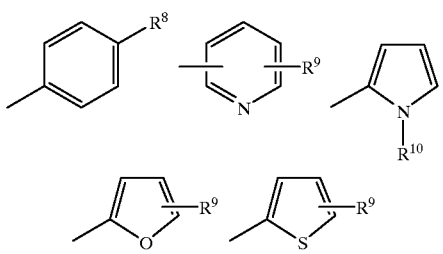

wherein R⁸ represents a C1–C2 alkoxy group, a C1–C2 haloalkoxy group, a C1–C2 alkylthio group, a nitro group or a cyano group; R⁹ represents a hydrogen atom, a hydroxyl group, a C1–C2 alkoxy group, a C1–C2 haloalkoxy group or a nitro group; and R¹⁰ represents a C1–C2 alkyl group.

7. A 1-aryl-3-cyano-5-(het)arylalkylaminopyrazole derivative according to claim 6, wherein R⁷ represents

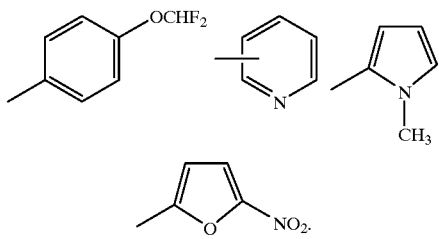

8. A 1-aryl-3-cyano-5-(het)arylalkylaminopyrazole derivative represented by the general formula (3):

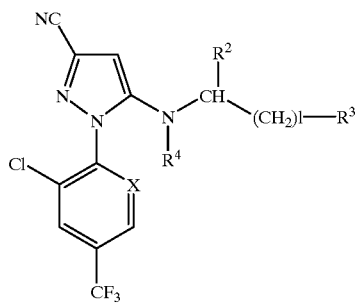

(3)

wherein R², R³, R⁴, X, and 1 are as shown in claim 1.

9. A 1-aryl-3-cyano-5-(het)arylalkylaminopyrazole derivative according to claim 1, characterized by being obtained by allowing a compound represented by the general formula (3):

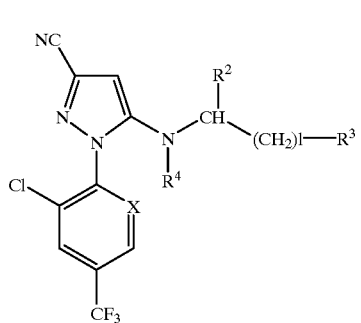

(3)

wherein R², R³, R⁴, X, and 1 are as shown in claim 1, to react with R¹S(O)$_n$—Y (wherein R¹ and n are as shown in claim 1; and Y represents a halogen atom, a hydroxyl group or a salt thereof, or a dialkylamino group).

10. A process for producing the compound claimed in claim 1, which is characterized by allowing a compound represented by the general formula (3):

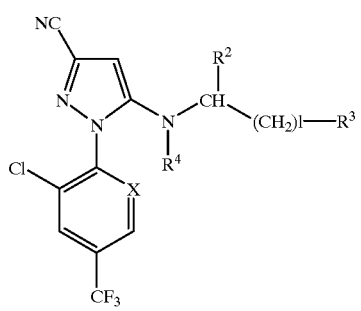

(3)

wherein R², R³, R⁴, X, and 1 are as shown in claim 1, to react with R¹S(O)$_n$—Y (wherein R¹ and n are as shown in claim 1; and Y represents a halogen atom, a hydroxyl group or a salt thereof, or a dialkylamino group).

11. A pesticide containing the 1-aryl-3-cyano-5-(het) arylalkylaminopyrazole derivative claimed in claim 1 as an active ingredient.

12. An insecticide containing the 1-aryl-3-cyano-5-(het) arylalkylaminopyrazole derivative claimed in claim 1 as an active ingredient.

13. An agricultural and horticultural insecticide containing the 1-aryl-3-cyano-5-(het)arylalkylaminopyrazole derivative claimed in claim 1 as an active ingredient.

14. The 1-aryl-3-cyano-5-(het)arylalkylaminopyrazole derivative according to claim 3, wherein

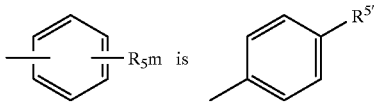

wherein $R^{5'}$ represents a C1–C2 alkoxy group, a C1–C2 haloalkoxy group, C1–C2 alkylthio group, a nitro group, or a cyano group.

15. The 1-aryl-3-cyano-5-(het)arylalkylaminopyrazole derivative according to claim 1, wherein $R^3$ is

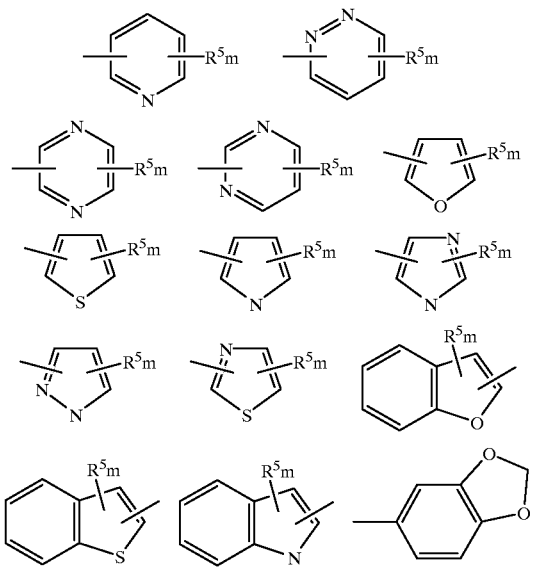

wherein $R^5$ represents a hydrogen atom, a hydroxyl group, a C1–C4 alkyl group, a C1–C8 haloalkyl group, a C1–C4 alkoxy group, a phenoxy group which may be substituted, a C1–C4 haloalkoxy group, a C1–C4 alkylthio group, a C1–C4 alkylsulfinyl group, a C1–C4 alkylsulfonyl group, a halogen atom, a nitro group, or a cyano group; and m represents 0, 1 or 2.

16. The 1-aryl-3-cyano-5-(het)arylalkylaminopyrazole derivative according to claim 4, wherein

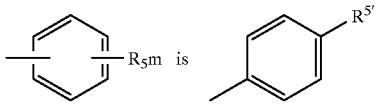

wherein $R^{5'}$ represents a C1–C2 alkoxy group, a C1–C2 haloalkoxy group, a C1–C2 alkylthio group, a nitro group, or a cyano group.

17. The 1-aryl-3-cyano-5-(het) arylalkylaminopyrazole derivative according to claim 1, wherein $R^3$ is

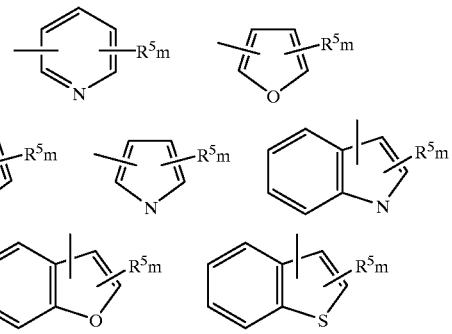

wherein $R^5$ represents a hydrogen atom, a hydroxyl group, a C1–C4 alkyl group, a C1–C8 haloalkyl group, a C1–C4 alkoxy group, a phenoxy group which may be substituted, a C1–C4 haloalkyl group, a C1–C4 alkylthio group, a C1–C4 alkylsulfinyl group, a C1–C4 alkylsulfonyl group, a halogen atom, a nitro group, or a cyano group; and m represents 0, 1 or 2.

18. The 1-aryl-3-cyano-5-(het)arylalkylaminopyrazole derivative according to claim 1, wherein $R^3$ is

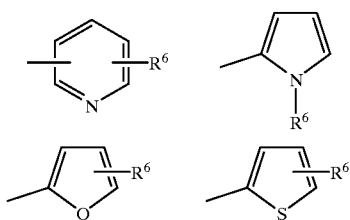

wherein $R^6$ represents a hydrogen atom, a hydroxyl group, a C1–C2 alkyl group, a C1–C2 alkoxy group, a C1–C2 haloalkyl group, a C1–C2 alkylthio group, a halogen atom, a nitro group, or a cyano group.

19. The 1-aryl-3-cyano-5-(het)arylalkylaminopyrazole derivative according Claim 6, wherein $R^7$ represents

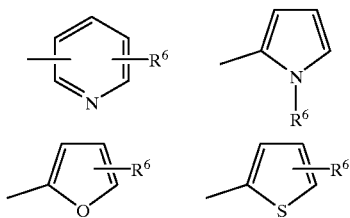

wherein $R^8$ represents a C1–C2 alkoxy group, a C1–C2 haloalkoxy group, a C1–C2 alkylthio group, a nitro group or a cyano group; $R^9$ represents a hydrogen atom, a hydroxyl group, a C1–C2 alkoxy group, a C1–C2 haloalkoxy group or nitro group; and $R^{10}$ represents a C1–C2 alkyl group.

20. The 1-aryl-3-cyano-5-(het)arylalkylaminopyrazole derivative according to claim 6, wherein $R^7$ represents

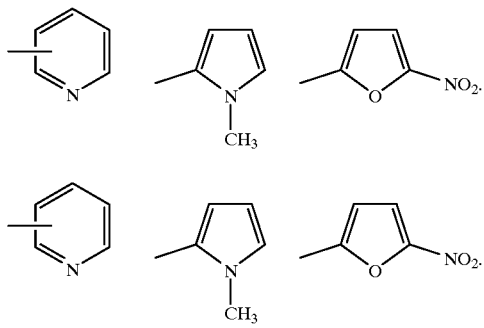
21. A process for producing the compound claimed in claim 1, comprising:
reacting a compound represented by formula (3):
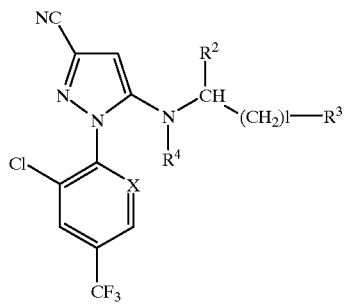
(3)
with $R^1S(O)_m$—Y;
  wherein $R^2$, $R^3$, $R^4$, X, and 1 are shown in claim 1
  wherein $R^1$ is as shown in Claim 1 and n is 0; and Y represents a halogen atom, a hydroxyl group or a salt thereof, or a dialkylamino group.
* * * * *